(12) United States Patent
Li et al.

(10) Patent No.: US 12,195,435 B2
(45) Date of Patent: Jan. 14, 2025

(54) 5-METHYLCHROMONE AND THE PREPARATION METHOD AND APPLICATION THEREOF

(71) Applicant: HAINAN MEDICAL UNIVERSITY, Haikou (CN)

(72) Inventors: Youbin Li, Haikou (CN); Xuesong Wang, Haikou (CN); Yan Wang, Haikou (CN); Junyu Xu, Haikou (CN); Yu Chen, Haikou (CN); Tingting Zeng, Haikou (CN); Xue Cui, Haikou (CN); Yinfeng Tan, Haikou (CN); Jingwen Gong, Haikou (CN)

(73) Assignee: HAINAN MEDICAL UNIVERSITY, Haikou (CN)

( * ) Notice: Subject to any disclaimer, the term of this patent is extended or adjusted under 35 U.S.C. 154(b) by 816 days.

(21) Appl. No.: 17/299,631

(22) PCT Filed: Mar. 12, 2021

(86) PCT No.: PCT/CN2021/080485
§ 371 (c)(1),
(2) Date: Jun. 3, 2021

(87) PCT Pub. No.: WO2022/088583
PCT Pub. Date: May 5, 2022

(65) Prior Publication Data
US 2022/0324824 A1 Oct. 13, 2022

(30) Foreign Application Priority Data
Oct. 27, 2020 (CN) .......................... 202011166791.7

(51) Int. Cl.
*C07D 311/22* (2006.01)
*A61K 8/49* (2006.01)
*A61Q 19/02* (2006.01)

(52) U.S. Cl.
CPC ............ *C07D 311/22* (2013.01); *A61K 8/498* (2013.01); *A61Q 19/02* (2013.01)

(58) Field of Classification Search
CPC ....... A61Q 19/02; A61K 8/498; C07D 311/22
See application file for complete search history.

(56) References Cited

PUBLICATIONS

Ahluwalia, Indian J of CHem, vol. 15B. Nov. 1977, 1003-1005. (Year: 1977).*

* cited by examiner

*Primary Examiner* — D Margaret M Seaman
(74) *Attorney, Agent, or Firm* — NIXON & VANDERHYE

(57) ABSTRACT

Disclosed is a 5-methylchromone and the preparation method and application thereof, the 5-methylchromone has the following structure:

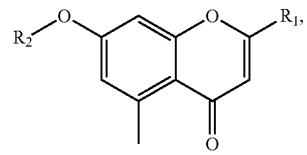

wherein R1 and R2 are alkyl groups. The substituted chromone has the biological activity of inhibiting tyrosinase. The preparation method uses 3,5-dihydroxytoluene as a raw material, and synthesis of chromones substituted with different groups at 2-C through acylation, esterification, rearrangement and cyclization reactions, etc. The 5-methyl-chromone is a completely new compound in condition that R1 is —CH$_2$CH$_2$CH$_3$, and R2 is —CH$_2$CH$_3$, or that R1 is —C(CH$_3$)$_3$, and R2 is H. All the compounds have obvious inhibitory activity against tyrosinase, and can be used to prepare tyrosinase inhibitors or whitening agents.

10 Claims, 10 Drawing Sheets

5-METHYLCHROMONE AND THE PREPARATION METHOD AND APPLICATION THEREOF

This application is the U.S. national phase of International Application No. PCT/CN2021/080485 filed Mar. 12, 2021 which designated the U.S. and claims priority to CN patent application No. 202011166791.7 filed Oct. 27, 2020, the entire contents of each of which are hereby incorporated by reference.

FIELD OF THE INVENTION

The invention relates to the technical field of whitening skin care products, in particular relates to a 5-methylchromone and the preparation method and application thereof.

BACKGROUND OF THE INVENTION

The use of whitening skin care products has a very long history, and has been passed down to this day with the existence and development of human beings. Fair skin and moisturizing are the pursuit of oriental female, so the whitening skin care products are quite popular among the people who care about their beauty. In the early days, people used physical covering for whitening (such as pressed powder, foundation, and whitening powder nectar, etc.). In the 1950s, they began to change to the physiological whitening which the mercury-based preparations were externally used to reduce melanin. Because mercury-based preparations can cause skin irritation and have a great impact on the central nervous system, causing people to have symptoms such as memory decline and insomnia, so mercury-based preparations were banned in the 1970s. Hydroquinone began to be used as whitening agent for cosmetics and external preparations for the treatment of pigmentation in dermatology at domestic and overseas in the 1960s, subsequently, it was found that the hydroquinone also produced many side effects while lightening the skin tone. Long-term use of hydroquinone could also cause exogenous leukoplakia and ochronosis. The European Union (EU) banned the addition of hydroquinone in cosmetics on Jan. 2, 2002. In recent years, with the continuous understanding of the biological mechanism of melanin formation, coupled with the safety problems of chemical whitening agents, it is promising to find safe and efficient whitening active substances from natural products, which has become the focus of cosmetics research.

Tyrosinase (monophenol or diphenol, oxidoreductase, EC1.14.18.1) is a combined 3-type multifunctional copper-containing glycoprotein that is located in the membrane of the melanosome. Tyrosinase is only produced by melanocytes, after it is produced and processed in the endoplasmic reticulum and Golgi apparatus, it is transported to the melanosome, where it catalyzes the synthesis of melanin. Therefore, regulating melanin synthesis by inhibiting tyrosinase is the main way to prevent pigmentation. Because tyrosinase is the key enzyme for melanin production by melanocytes, directly inhibiting the catalytic activity of tyrosinase is the most prominent and effective target for inhibiting melanin production, most cosmetic whitening agents on the market are mostly tyrosinase inhibitors.

Aloe contains an important chromone—aloesin, which reduces the formation of melanin by competitively inhibiting tyrosinase at a non-cytotoxic concentration, thereby whitening the skin; the whitening and UV-B protective effect of aloesin has also been clinically verified, so the aloesin is used as a whitening agent in the cosmetics industry. However, the content of aloesin in aloe is extremely low, and the content of aloesin in Curacao aloe with high content is only 0.32%. The cost of separation and purification is too high. On the other hand, because it is difficult to synthesize the C-glycosyl moiety in the molecule, industrialization is not easy, which limits the wide application of aloesin.

BRIEF SUMMARY OF THE INVENTION

In view of this, the present invention proposes a 5-methylchromone and the preparation method and application thereof.

The technical solutions of the present invention are realized as follows:

A 5-methylchromone, having the structure shown in formula (1):

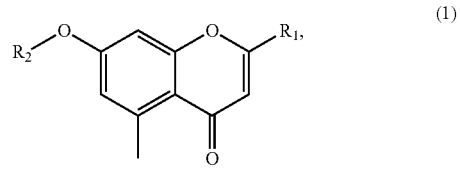

where the R1 is —$CH_2CH_2CH_3$ and —$C(CH_3)_3$, and R2 is H and —$CH_2CH_3$.

Further, its structure is as shown in the formula (1-6):

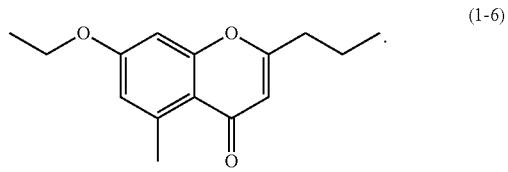 [SMILES: CCCc1cc(=O)c2c(C)cc(OCC)cc2o1]

Further, its structure is as shown in the formula (1-4):

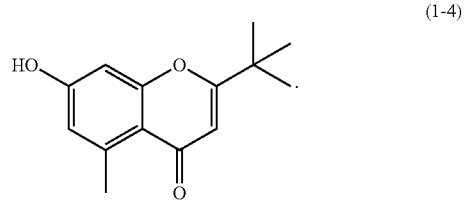 [SMILES: Cc1cc(O)cc2oc(C(C)(C)C)cc(=O)c12]

A preparation method of 5-methylchromone, having reaction formula:

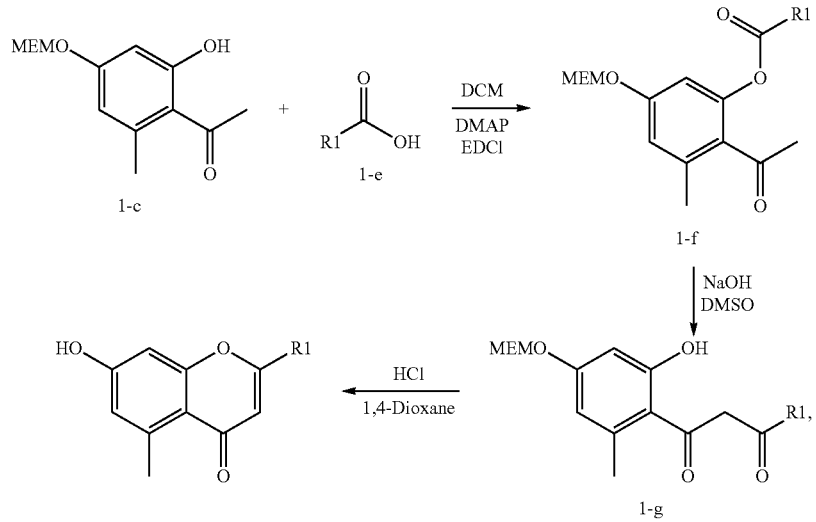

where R1 is —CH$_3$, —CH$_2$CH$_3$, —CH$_2$CH$_2$CH$_3$, —C(CH$_3$)$_3$;
the preparation method comprising:
dissolving the compound 1-c and the compound 1-e in the DCM (Dichloromethane), adding the DMAP(4-dimethylaminopyridine), cooling to 0° C., then adding EDCI (1-ethyl-(3-dimethylaminopropyl) carbodiimide hydrochloride, N-(3-(Dimethylamino)propyl)-N'-ethylcarbodiimide hydrochloride), raising to room temperature, and stirring to react; after the reaction being completed, extracting with ethyl acetate and water, taking the organic phase, concentrating under reduced pressure, and separating and purifying the residue by column chromatography, the purification solvent A being petroleum ether and ethyl acetate, obtaining the compound 1-f;
dissolving the compound 1-f in DMSO (dimethyl sulfoxide), adding NaOH (sodium hydroxide), stirring to react; after the reaction being completed, extracting with ethyl acetate and water, taking the organic phase, concentrating under reduced pressure, and separating and purifying the residue by column chromatography; purification solvent B being petroleum ether and ethyl acetate to obtain the compound 1-g.
dissolving compound 1-g in 1,4-Dioxane (1,4-Dioxane), dropping concentrated hydrochloric acid (HCl) solution, stirring to react; after the reaction being completed, concentrating under reduced pressure, and washing the residue with dichloromethane to obtain the target compound; wherein,
in case that R1 is —CH$_3$, it is obtained for a target compound 1-1; R1 being —CH$_2$CH$_3$, obtained a target compound 1-2;
in case that R1 is —CH$_2$CH$_2$CH$_3$, it is obtained a compound 1-3; R1 being —C(CH$_3$)$_3$, obtained the target compound 1-4.
Further, in condition that the R1 is —CH$_3$, —CH$_2$CH$_3$, —CH$_2$CH$_2$CH$_3$, the purification solvent A is prepared by petroleum ether and ethyl acetate in a volume ratio of 7:1; the purification solvent B is prepared by petroleum ether and ethyl acetate in a volume ratio of 6:1;
in condition that the R1 is —C(CH$_3$)$_3$, the purification solvent A is prepared by petroleum ether and ethyl acetate in a volume ratio of 8:1; the purified solvent B is prepared by petroleum ether and ethyl acetate in a volume ratio of 7:1.

A preparation method of 5-methylchromone, having reaction formula:

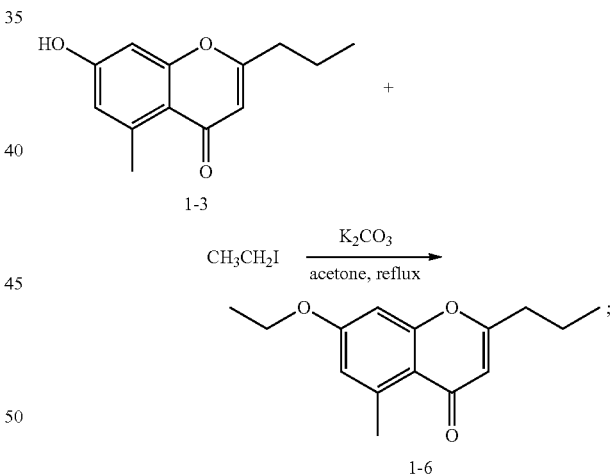

the preparation method comprising:
dissolving the compound 1-3 and iodomethane in acetone, adding K$_2$CO$_3$, heating to reflux and stirring to react; after the reaction being completed, concentrating under reduced pressure, and separating and purifying the residue by column chromatography, the purification solvents being petroleum ether and ethyl acetate, obtaining the target compound 1-6.

A preparation method of 5-methylchromone, wherein the compound 1-3 of the present invention is reacted with iodomethane to obtain a compound 1-5, having reaction formula:

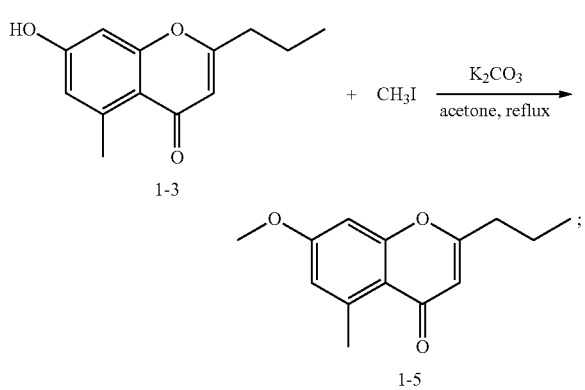

the preparation method comprising:

dissolving the compound 1-3 and iodomethane in acetone, adding $K_2CO_3$, heating to reflux and stirring to react; after the reaction being completed, concentrating under reduced pressure, and separating and purifying the residue by column chromatography, the purification solvents being petroleum ether and ethyl acetate to obtain the target compound 1-5.

A tyrosinase inhibitor or whitening agent comprising a compound as shown in the formula (1)

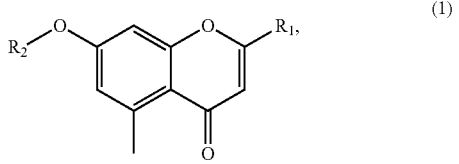

(1)

wherein the R1 is —$CH_3$, —$CH_2CH_3$, —$CH_2CH_2CH_3$ and —$C(CH_3)_3$, and R2 is H, —$CH_3$ and —$CH_2CH_3$.

A tyrosinase inhibitor or whitening agent comprising the compound having the formula (1-6).

A tyrosinase inhibitor or whitening agent comprising the compound having the formula (1).

Compared with the prior art, the present invention has the following beneficial effects:

(1) The present invention synthesizes the aglycon derivative (5-methylchromone) of aloesin, which is easy to synthesize and has similar to or stronger than tyrosinase inhibitory activity with aloesin. To provide a high-quality and low-cost whitening raw material for the whitening skin care product market is of great significance to the whitening skin care product industry.

(2) The substituted series of chromones of the present invention have obvious inhibitory activity against tyrosinase, and can be used as basic raw materials for whitening and skin care by monomers or complexes, and can be used for preparing tyrosinase inhibitors or whitening agents with high safety, and can be better used in the field of whitening and skin care products.

(3) In the present invention, the 5-methylchromone is a completely new compound in condition that R1 is —$CH_2CH_2CH_3$, and R2 is —$CH_2CH_3$, or that R1 is —$C(CH_3)_3$, and R2 is H.

(4) The preparation method of the present invention uses 3,5-dihydroxytoluene as the raw material, by means of acylation, esterification, rearrangement, and cyclization reaction and etc., synthesize chromones substituted with different groups at the 2-C, obtain a series of chromones with tyrosinase inhibitory activity; then use haloalkane to modify the 7-hydroxyl group to further increase the inhibition rate of tyrosinase. In addition, the present invention uses high-concentration hydrochloric acid to complete the cyclization reaction and deprotection at the same time, eliminating the trouble of using ion exchange resins.

DETAILED DESCRIPTION OF THE INVENTION

Figure 1:
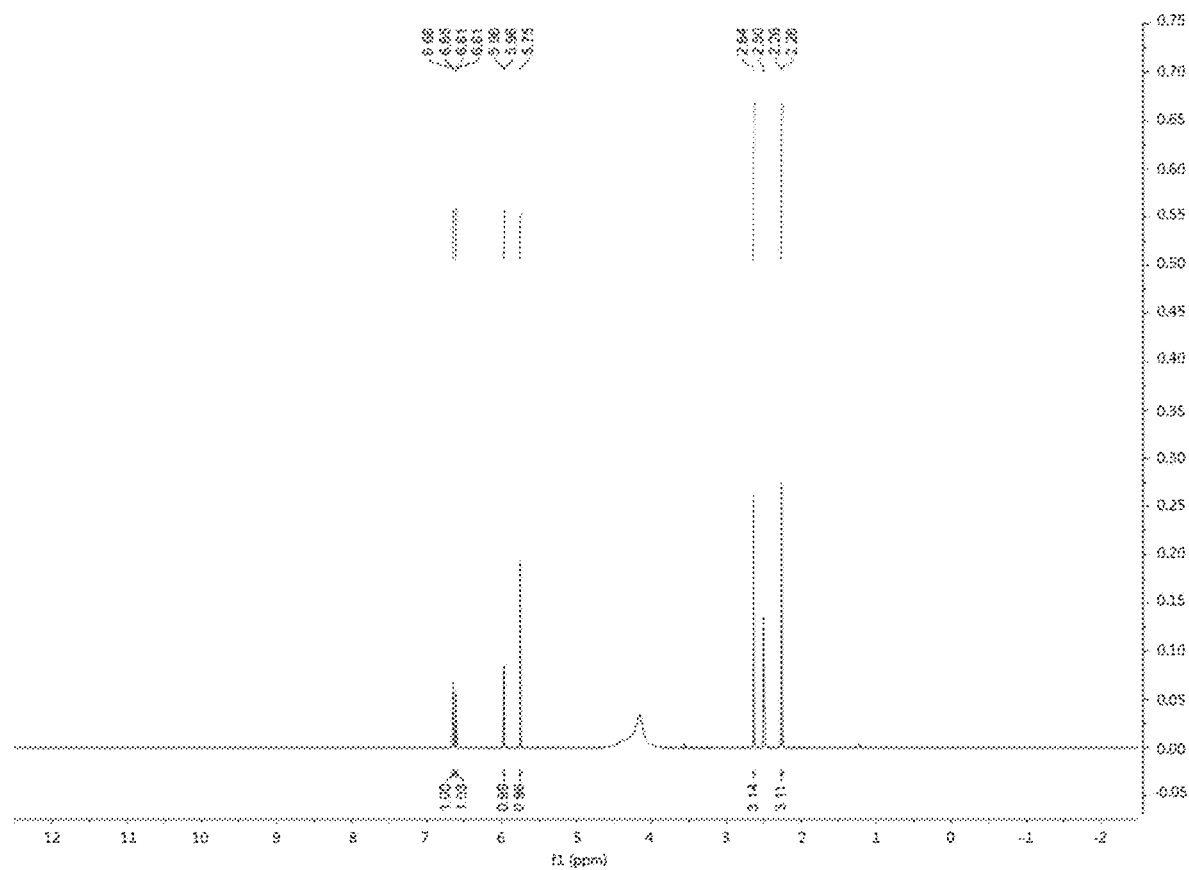
FIG. 1 shows the $^1$H NMR chart of compound 1-1 of the present invention.
Figure 2:
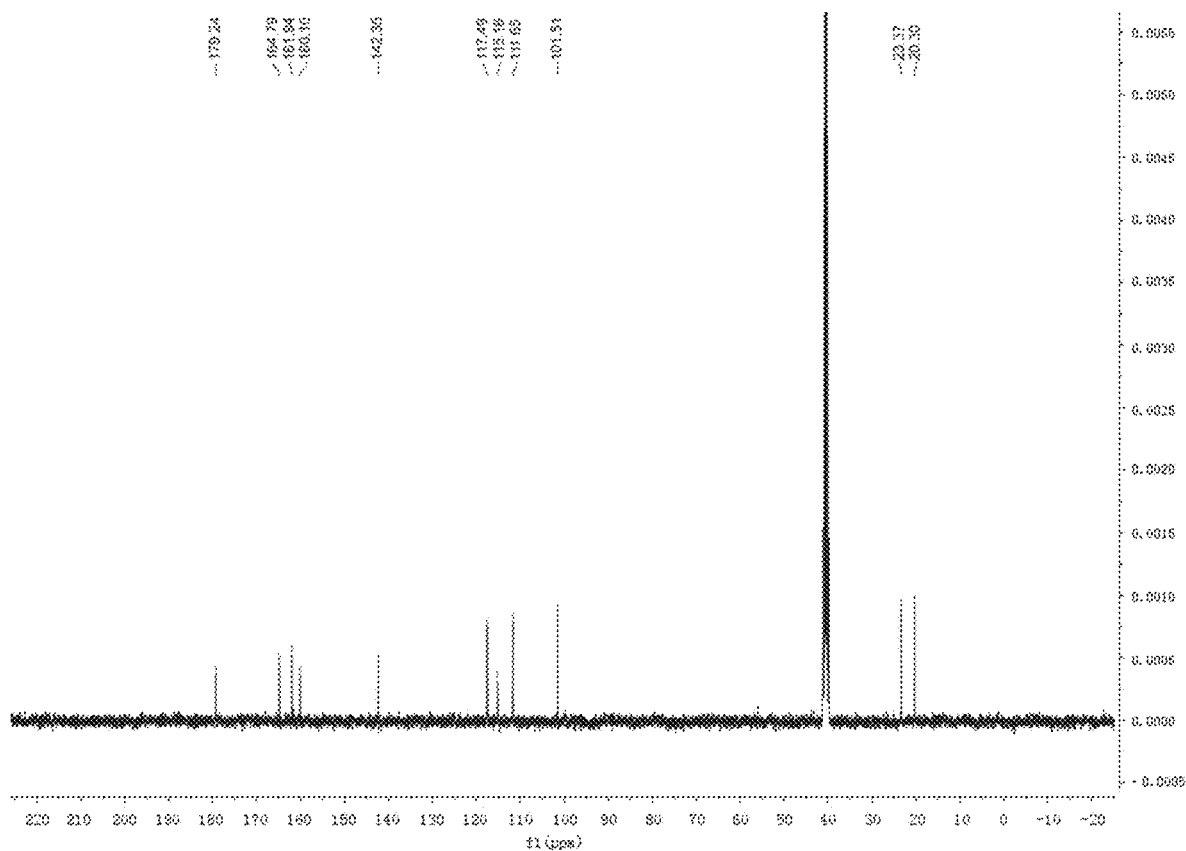
FIG. 2 shows the $^{13}$C NMR chart of compound 1-1 of the present invention.
Figure 3:
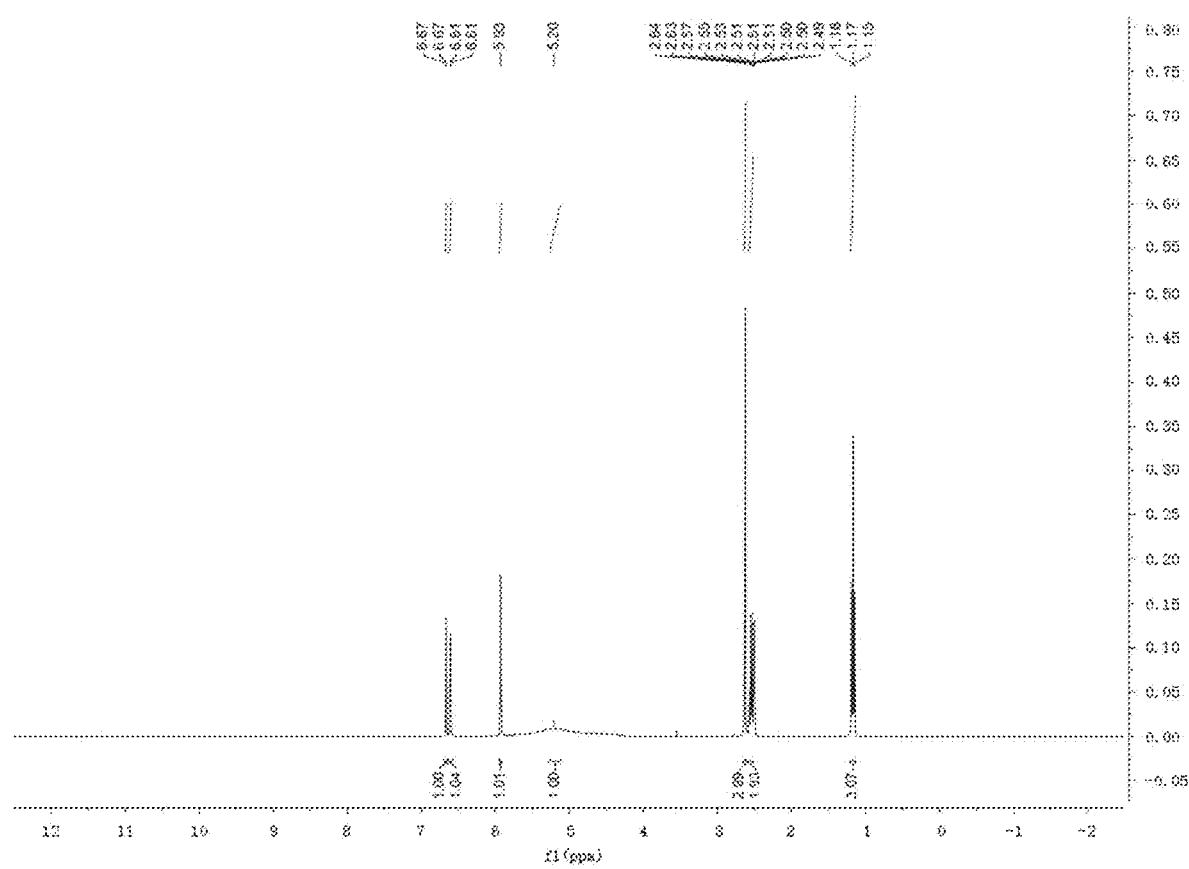
FIG. 3 shows the $^1$H NMR chart of compound 1-2 of the present invention.
Figure 4:
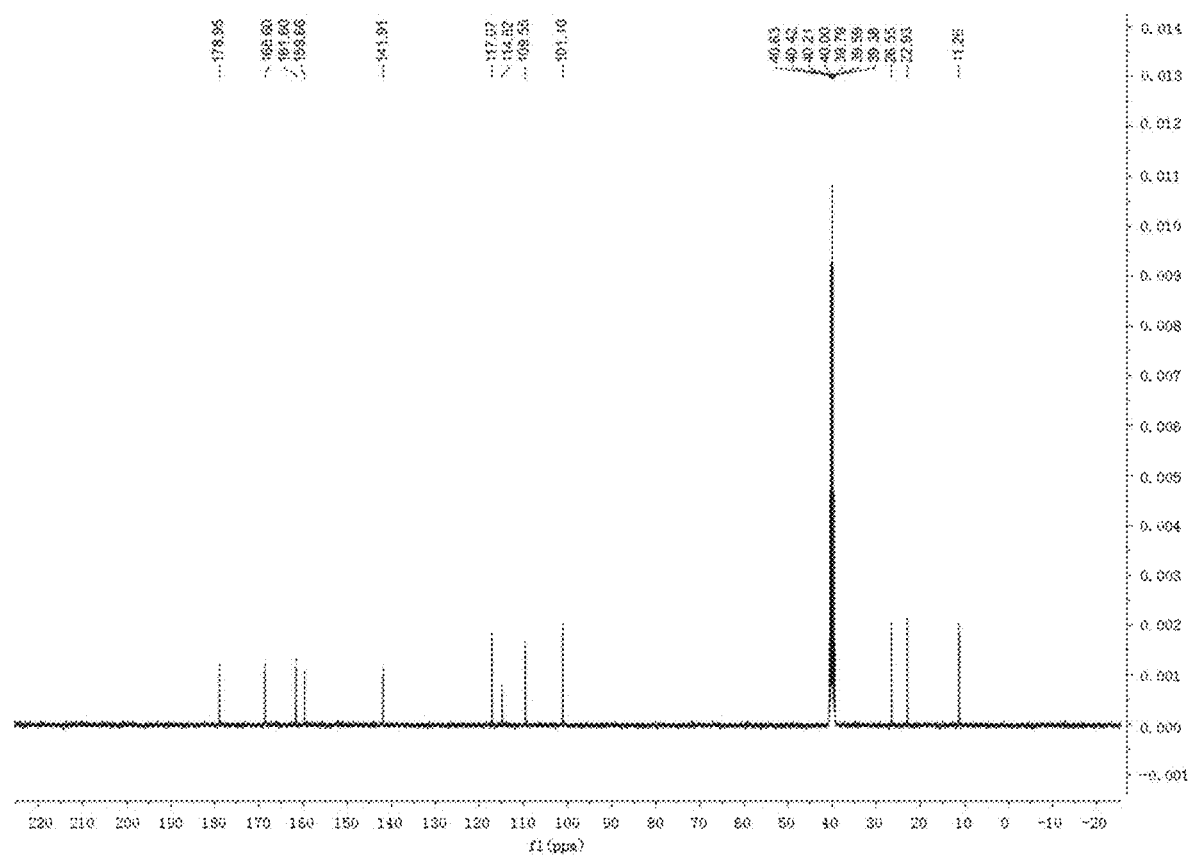
FIG. 4 shows the $^{13}$C NMR chart of compound 1-2 of the present invention.
Figure 5:
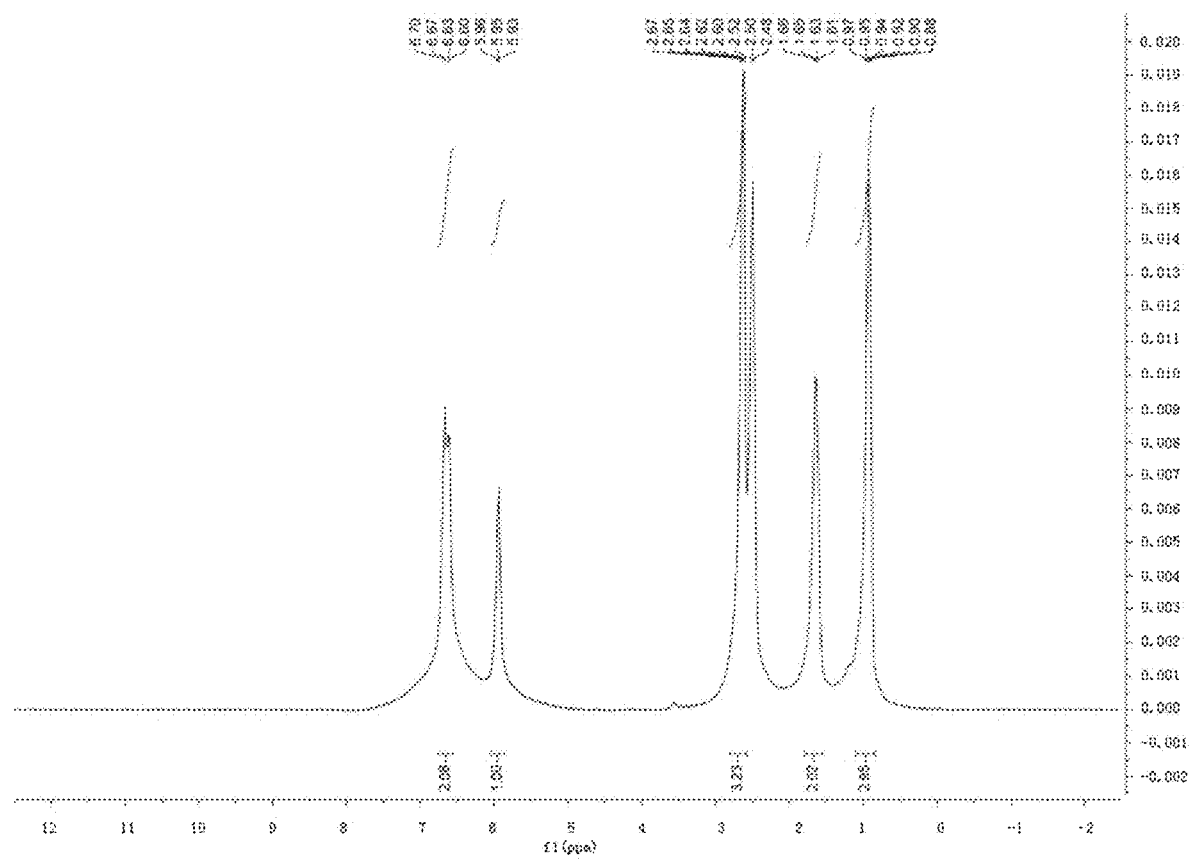
FIG. 5 shows the $^1$H NMR chart of compound 1-3 of the present invention.
Figure 6:
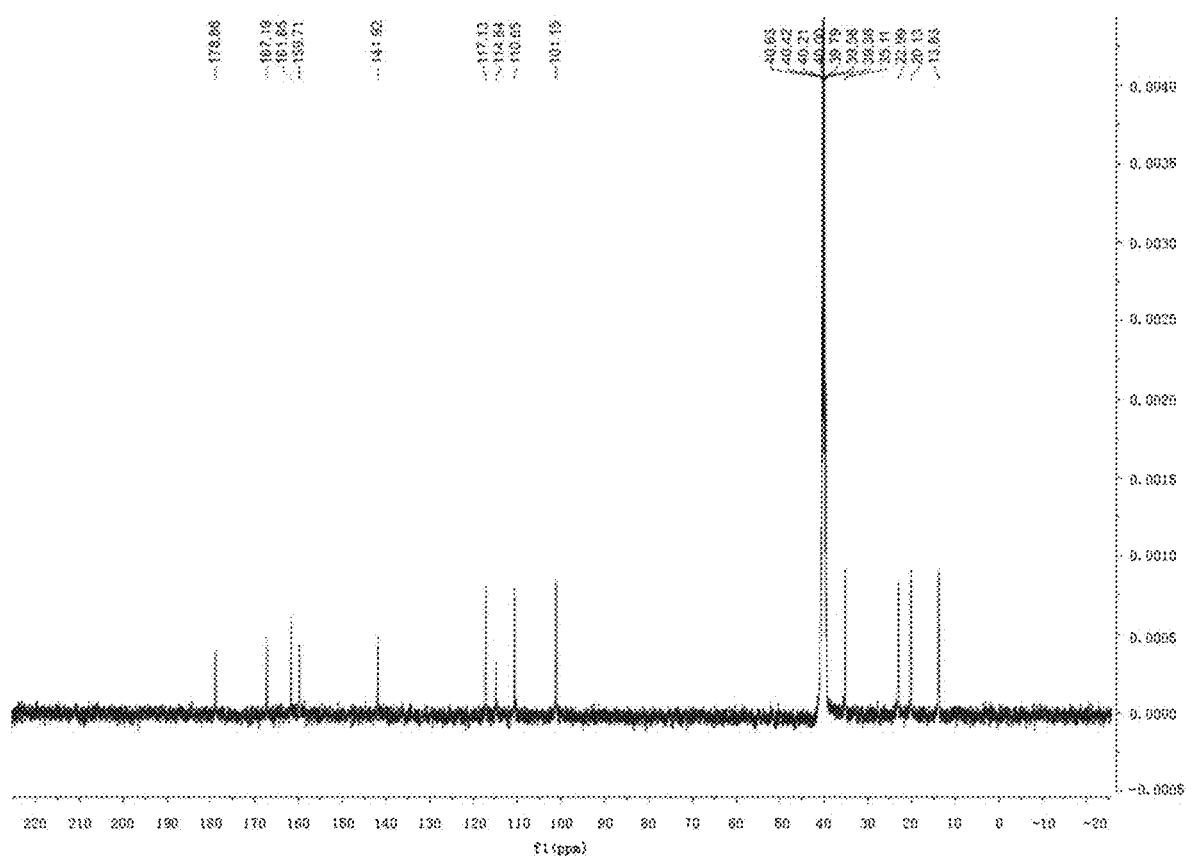
FIG. 6 shows the $^{13}$C NMR chart of compound 1-3 of the present invention.
Figure 7:
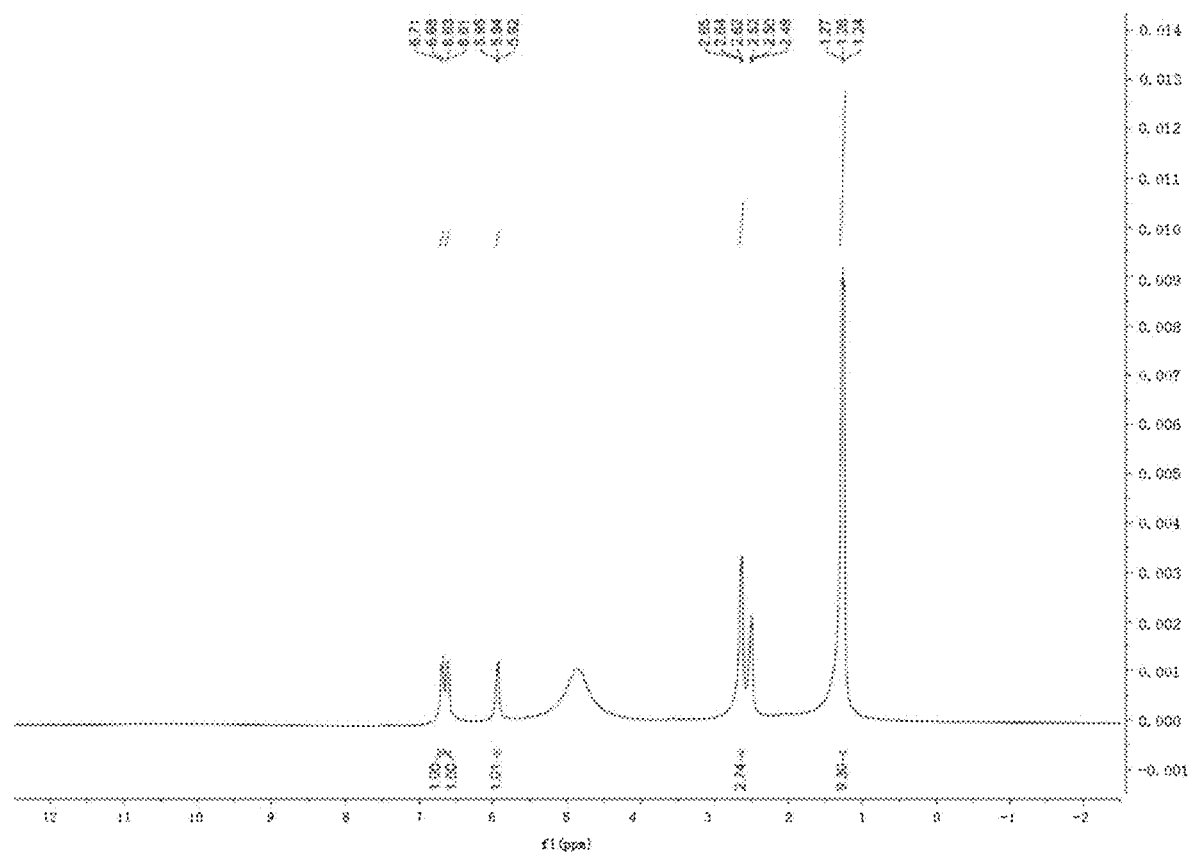
FIG. 7 shows the $^1$H NMR chart of compound 1-4 of the present invention.
Figure 8:
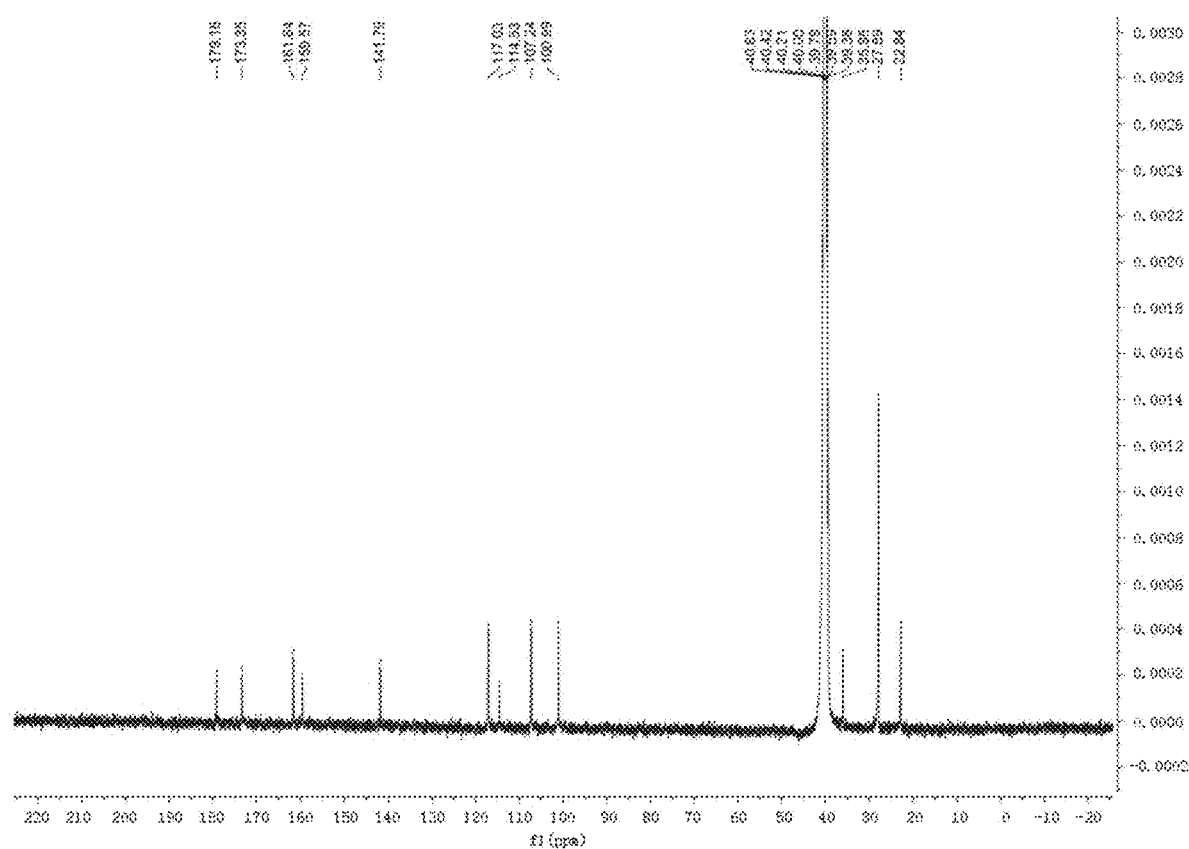
FIG. 8 shows the $^{13}$C NMR chart of compound 1-4 of the present invention.
Figure 9:
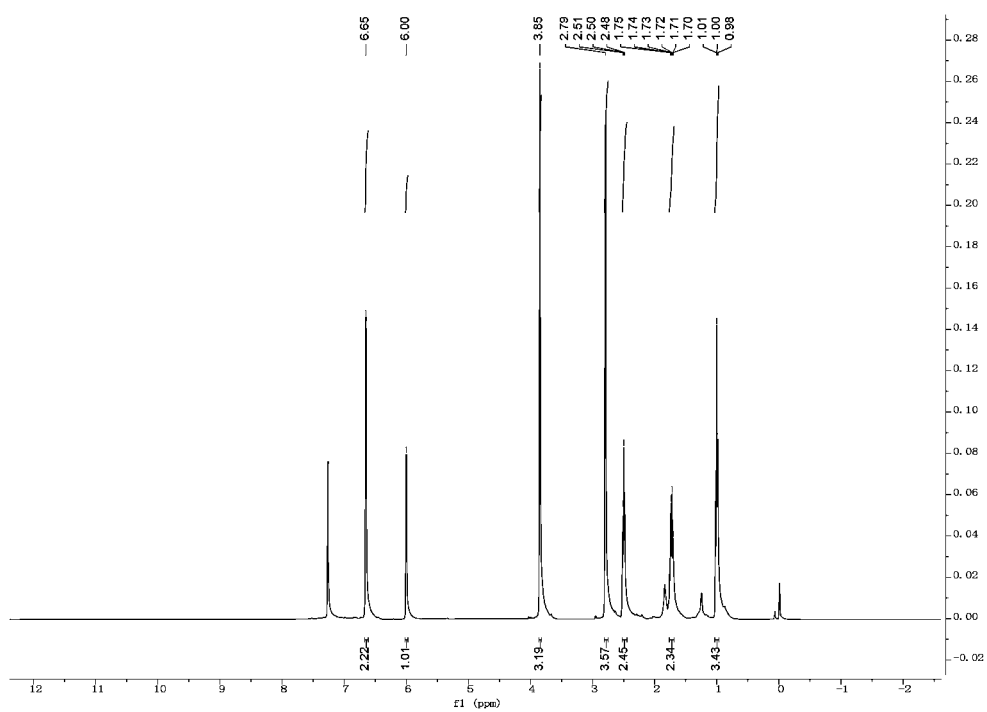
FIG. 9 shows the $^1$H NMR chart of compound 1-5 of the present invention.
Figure 10:
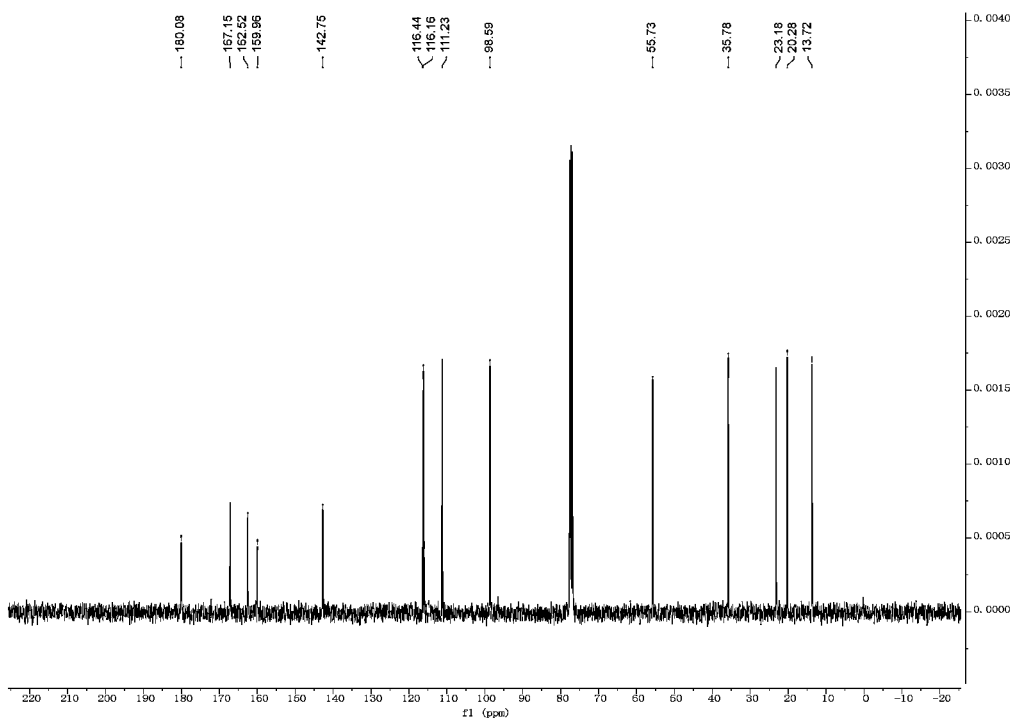
FIG. 10 shows the $^{13}$C NMR chart of compound 1-5 of the present invention.
Figure 11:
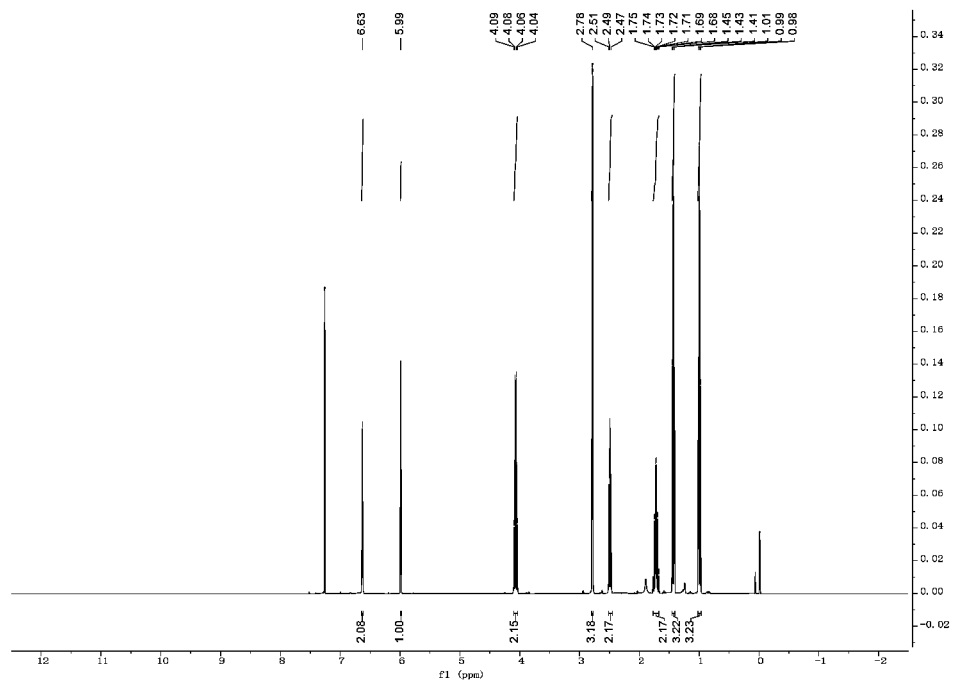
FIG. 11 shows the $^1$H NMR chart of compound 1-6 of the present invention.
Figure 12:
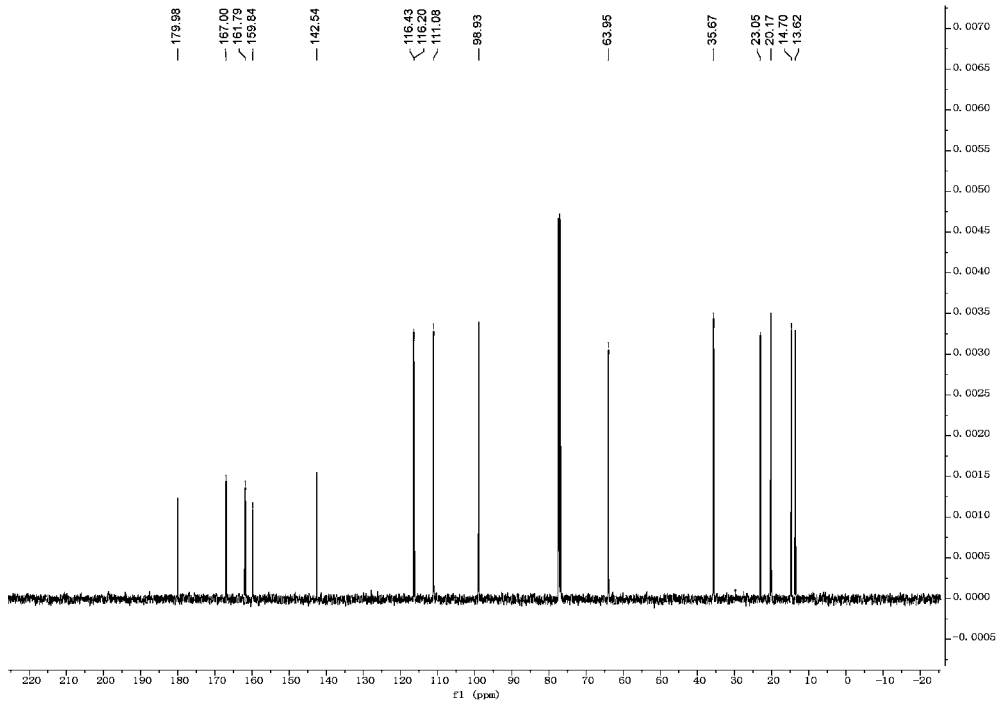
FIG. 12 shows the $^{13}$C NMR chart of compound 1-6 of the present invention.

In order to better understand the technical content of the present invention, specific embodiments are provided below to further illustrate the present invention.

Unless otherwise specified, the experimental methods used in the embodiments of the present invention are conventional methods.

The materials, reagents, etc. used in the embodiments of the present invention can be obtained from commercial sources unless otherwise specified.

1. Synthesis of Target Compound
Synthesis of Compound 1-b

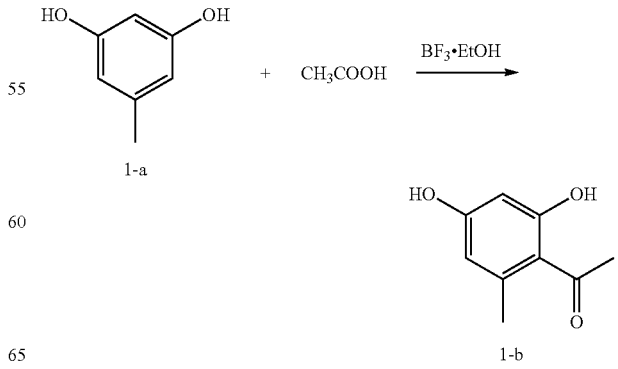

Adding the compound 1-a (10 mmol, 1.24 g), anhydrous acetic acid (70 mmol, 4 mL) and boron trifluoride etherate (21 mmol, 2.6 mL) into a 25 mL round bottom flask, and heating to 80° C. and magnetically stirring to react for 12 h; after the reaction being completed, cooling to room temperature, then extracting with ethyl acetate and water twice, taking the organic phase, washing with saturated sodium bicarbonate solution for three times until no bubbles being generated, and then washing with saturated salt aqueous solution once, drying with anhydrous sodium sulfate, concentrating under reduced pressure, then performing the recrystallization, obtaining the compound 1-b (0.99 g, yield 60%) as a yellowish white powder.

Synthesis of Compound 1-c

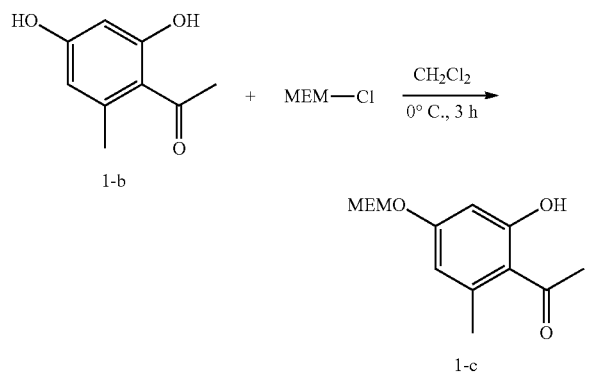

Dissolving the compound 1-b (10 mmol, 1.66 g) in 10 mL of dichloromethane, and cooling to 0° C. with an ice bath, slowly dropping MEM-Cl (12 mmol, 1.36 mL), then the temperature being raised naturally, and magnetic stirring to reaction for 3 h; after the reaction being completed, directly concentrating under reduced pressure to remove the solvent. separating and purifying the residue by column chromatography (petroleum ether:ethyl acetate=7:1, v/v), obtaining a colorless oily liquid compound 1-c (2.28 g, yield 90%).

Synthesis of Compound 1-1

Dissolving compound the 1-c (10 mmol, 2.54 g) and compound the 1-e-1 (12 mmol, 0.72 g) in 20 mL of dichloromethane and placing them in a 50 mL round bottom flask, then adding DMAP (2 mmol, 0.244 g), cooling to 0° C., then adding EDCI (20 mmol, 3.82 g), naturally rising to room temperature, and magnetic stirring to reaction for 6 h; after the reaction being completed, extracting with ethyl acetate and water, taking the organic phase, concentrating under reduced pressure, and separating and purifying the residue by column chromatography, obtaining a colorless oily liquid compound 141 (2.66 g, yield 90%).

Dissolving the compound 141 (10 mmol, 2.96 g) in 10 mL of DMSO, adding NaOH (24 mmol, 0.96 g), magnetic stirring at room temperature for 4 h; after the reaction being completed, extracting with ethyl acetate and water for three times, taking the organic phase, concentrating under reduced pressure, and separating and purifying the residue by column chromatography (petroleum ether:ethyl acetate=6:1, v/v) obtaining a yellow oily liquid compound 1-g-1 (2.66 g, 90% yield).

Dissolving the compound 1-g-1 (10 mmol, 3.82 g) in 20 mL of 1,4-dioxane, dripping a catalytic amount of concentrated hydrochloric acid solution, and magnetic stirring at room temperature for 6 h; after the reaction being completed, concentrating under reduced pressure, washing the white solid residue with dichloromethane, obtaining a white powdery solid compound 1-1 (1.65 g, yield 87%).

Nuclear magnetic data of the compound 1-1: white solid powder, $^1$H NMR (400 MHz, CDCl$_3$) δ 6.65 (d, J=4 Hz, 1H), 6.61 (s, 1H), 5.96 (s, 1H), 5.75 (s, 1H), 2.64 (s, 3H), 2.26 (s, 3H); $^{13}$C NMR (100 MHz, CDCl$_3$) δ 179.24, 164.79, 161.94, 160.10, 142.35, 117.49, 115.16, 111.65, 101.51, 23.37, 20.30.

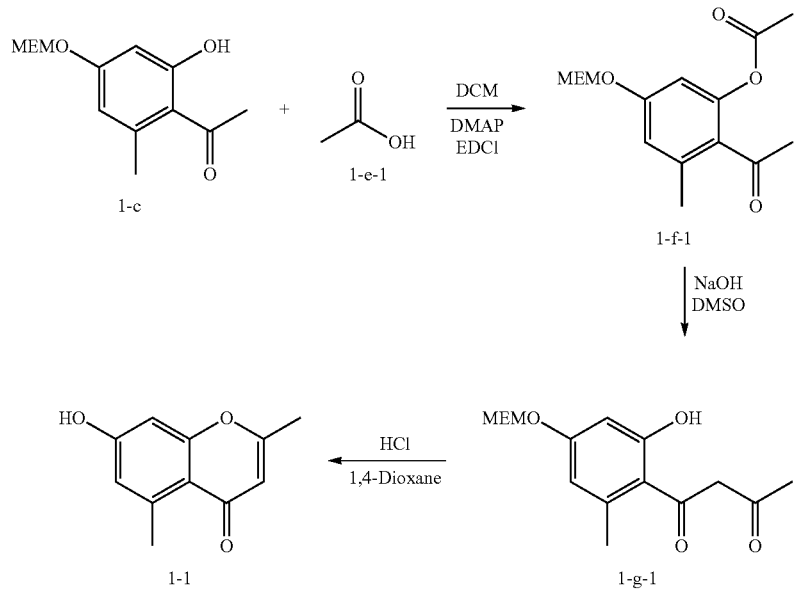

Synthesis of Compound 1-2

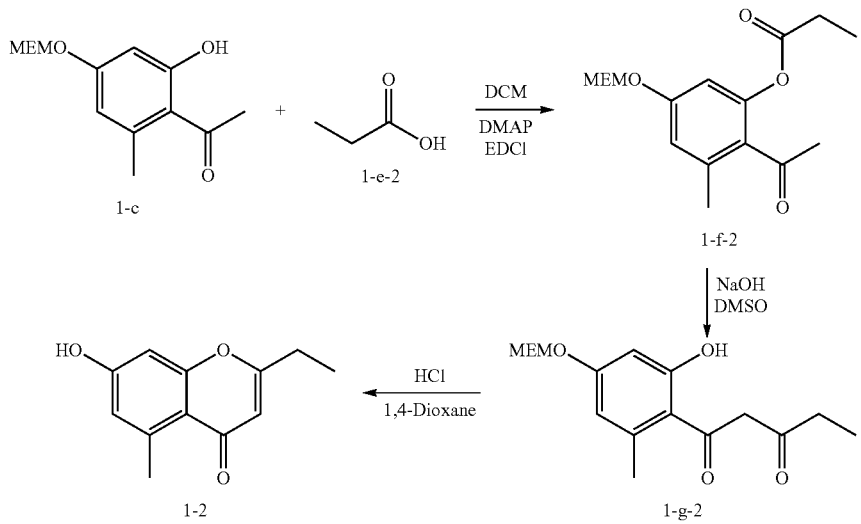

Dissolving the compound 1-c (10 mmol, 2.54 g) and the compound 1-e-2 (12 mmol, 0.88 g) in 20 mL of dichloromethane and placing in a 50 mL round bottom flask, adding DMAP (2 mmol, 0.244 g), cooling to 0° C., then adding EDCI (20 mmol, 3.82 g), naturally rising to room temperature, and magnetically stirring to react for 6 h; after the reaction being completed, extracting with ethyl acetate and water, taking the organic phase, concentrating under reduced pressure, and separating and purifying the residue by column chromatography (petroleum ether:ethyl acetate=7:1, v/v) obtaining a colorless oily liquid compound 1-f-2 (3.07 g, yield 99%).

Dissolving the compound 1-f-2 (10 mmol, 3.10 g) in 10 mL of DMSO, adding NaOH (24 mmol, 0.96 g), and magnetic stirring at room temperature for 4 h; after the reaction being completed, extracting with ethyl acetate and water for three times, taking the organic phase, concentrating under reduced pressure, and separating and purifying the residue by column chromatography (petroleum ether:ethyl acetate=6:1, v/v), obtaining a yellow oily liquid compound 1-g-2 (2.85 g, yield 92%).

Dissolving the compound 1-g-2 (10 mmol, 3.10 g) in 20 mL of 1,4-dioxane, dripping a catalytic amount of concentrated hydrochloric acid solution, and magnetic stirring at room temperature for 6 h; after the reaction being completed, concentrating under reduced pressure, washing the white solid residue with dichloromethane, obtaining a white powdery solid 1-2 (1.73 g, yield 85%).

Nuclear magnetic data of the compound 1-2: white solid powder, $^1$H NMR (400 MHz, CDCl$_3$) δ 6.67 (s, 1H), 6.61 (s, 1H), 5.93 (s, 1H), 5.20 (s, 1H), 2.64 (d, J=4 Hz, 3H), 2.55 (t, J=8 Hz, 2H), 1.17 (t, J=8 Hz, 3H); $^{13}$C NMR (100 MHz, CDCl$_3$) δ 178.95, 168.60, 161.60, 159.66, 141.91, 117.07, 114.82, 109.55, 101.10, 26.55, 22.93, 11.26.

Synthesis of Compound 1-3

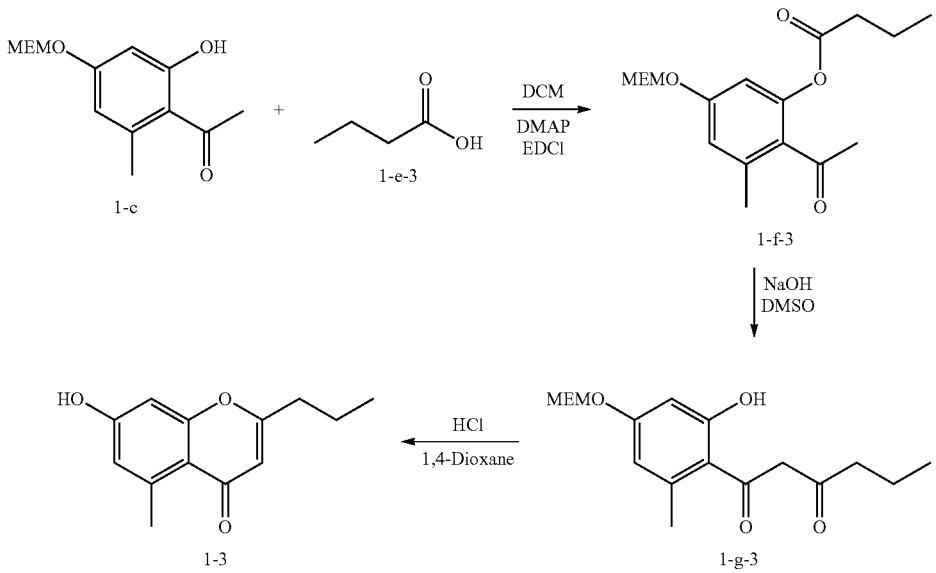

Dissolving the compound 1-c (10 mmol, 2.54 g) and the compound 1-e-3 (12 mmol, 1.05 g) in 20 mL of dichloromethane and placing them in a 50 mL round bottom flask, then adding DMAP (2 mmol, 0.244 g), cooling to 0° C., then adding EDCI (20 mmol, 3.82 g), naturally rising to room temperature, and magnetically stirring to react for 6 h; after the reaction being completed, extracting with ethyl acetate and water, taking the organic phase, concentrating under reduced pressure, and separating and purifying the residue by column chromatography (petroleum ether:ethyl acetate=7:1, v/v), obtaining a colorless oily liquid compound 1-f-3 (3.20 g, yield 99%).

Dissolving the compound 1-f-3 (10 mmol, 3.24 g) in 10 mL of DMSO, adding NaOH (24 mmol, 0.96 g), and magnetic stirring at room temperature for 4 h; after the reaction being completed, extracting with ethyl acetate and water for three times, taking the organic phase, concentrating under reduced pressure, and separating and purifying the residue by column chromatography (petroleum ether:ethyl acetate=6:1, v/v), obtaining a yellow oily liquid compound 1-g-3 (2.91 g, yield 90%).

Dissolving the compound 1-g-3 (10 mmol, 3.24 g) in 20 mL of 1,4-dioxane, dropping a catalytic amount of concentrated hydrochloric acid solution, and magnetic stirring at room temperature for 6 h; after the reaction being completed, concentrating under reduced pressure, washing the white solid residue with dichloromethane, obtaining a white powdery solid 1-3 (1.91 g, yield 88%).

Nuclear magnetic data of compound 1-3: white solid powder, $^1$H NMR (400 MHz, CDCl$_3$) δ 6.66 (s, 1H), 6.61 (s, 1H), 5.93 (s, 1H), 2.67-2.60 (m, 3H), 1.65 (s, 2H), 0.94 (s, 3H); $^{13}$C NMR (100 MHz, CDCl$_3$) δ 178.88, 167.19, 161.65, 159.71, 141.92, 117.13, 114.84, 110.65, 101.15, 22.99, 20.13, 13.83.

Synthesis of Compounds 1-4

Dissolving the compound 1-c (10 mmol, 2.54 g) and the compound 1-e-4 (12 mmol, 1.22 g) in 20 mL of dichloromethane and placing them in a 50 mL round bottom flask, then adding DMAP (2 mmol, 0.244 g), cooling to 0° C., then adding EDCI (20 mmol, 3.82 g), naturally rising to room temperature, and magnetic stirring to reaction for 6 h; after the reaction being completed, extracting with ethyl acetate and water, taking the organic phase, concentrating under reduced pressure, and separating and purifying the residue by column chromatography (petroleum ether:ethyl acetate=8:1, v/v), obtaining a colorless oily liquid compound 1-f-4 (3.04 g, yield 90%).

Dissolving the compound 1-f-4 (10 mmol, 3.38 g) in 10 mL of DMSO, adding NaOH (24 mmol, 0.96 g), and magnetic stirring at room temperature for 4 h; after the reaction being completed, extracting with ethyl acetate and water for three times, taking the organic phase, concentrating under reduced pressure, and separating and purifying the residue by column chromatography (petroleum ether:ethyl acetate=7:1, v/v) obtaining a yellow oily liquid compound 1-g-4 (3.04 g, yield 90%).

Dissolving the compound 1-g-4 (10 mmol, 3.38 g) in 20 mL of 1,4-dioxane, dripping a catalytic amount of concentrated hydrochloric acid solution, and magnetic stirring at room temperature for 6 h; after the reaction is completed, concentrating under reduced pressure, washing the white solid residue with dichloromethane, obtaining a white powdery solid 1-4 (1.97 g, yield 85%).

Nuclear magnetic data of compound 1-3: white solid powder, $^1$H NMR (400 MHz, CDCl$_3$) δ 6.67 (s, 1H), 6.61 (s, 1H), 5.93 (s, 1H), 5.20 (s, 1H), 2.64 (d, J=4 Hz, 3H), 2.55 (t, J=8 Hz, 2H), 1.17 (t, J=8 Hz, 3H); $^{13}$C NMR (100 MHz, CDCl$_3$) δ 178.95, 168.60, 161.60, 159.66, 141.91, 117.07, 114.82, 109.55, 101.10, 26.55, 22.93, 11.26.

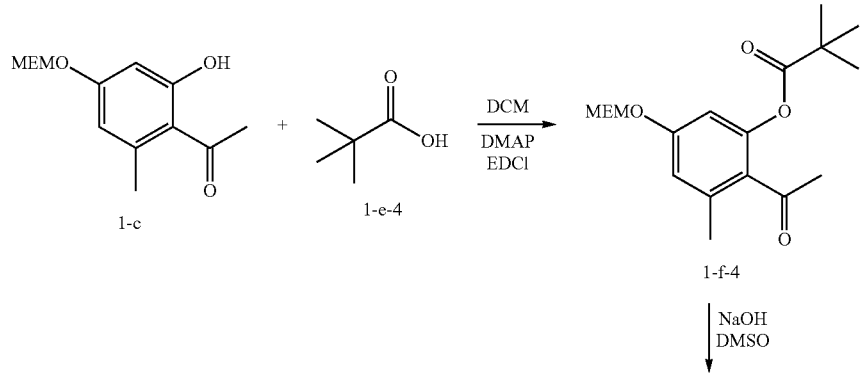

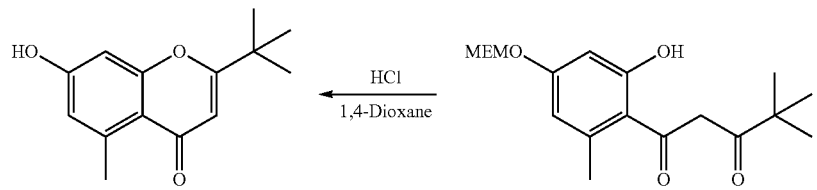

Synthesis of Compound 1-5

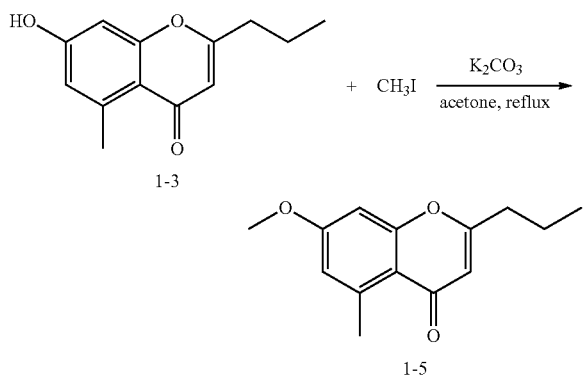

Dissolving the compound 1-3 (10 mmol, 2.18 g) and iodomethane (12 mmol, 1.70 g) in 20 mL of acetone and placing them in a 50 mL round bottom flask, then adding $K_2CO_3$ (12 mmol, 1.66 g), heating reflux and magnetically stirring to react for 2 h; after the reaction being completed, concentrating under reduced pressure, and separating and purifying the residue by column chromatography (petroleum ether:ethyl acetate=6:1, v/v), obtaining colorless oily liquid compound 1-5 (2.27 g, yield 98%).

Nuclear magnetic data of compound 1-5: $^1H$ NMR (400 MHz, CDCl3) δ 6.65 (s, 2H), 6.00 (s, 1H), 3.85 (s, 3H), 2.79 (s, 3H), 2.50 (t, J=4 Hz, 8 Hz, 2H), 1.75-1.70 (m, 2H), 1.00 (t, J=4 Hz, 8 Hz, 3H); $^{13}C$ NMR (100 MHz, CDCl3) δ180.08, 167.15, 162.52, 159.96, 142.74, 116.44, 116.16, 111.23, 98.59, 55.73, 35.78, 23.18, 20.28, 13.72.

Synthesis of Compound 1-6

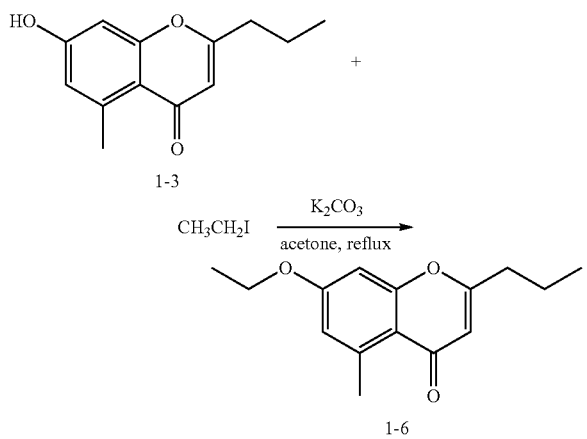

Dissolving the compound 1-3 (10 mmol, 2.18 g) and iodoethane (12 mmol, 1.87 g) in 20 mL of acetone and placing them in a 50 mL round bottom flask, then adding $K_2CO_3$ (12 mmol, 1.66 g), heating reflux and magnetically stirring to react for 2 h; after the reaction being completed, concentrating under reduced pressure, and separating and purifying the residue by column chromatography (petroleum ether:ethyl acetate=6:1, v/v), obtaining colorless oily liquid 1-6 (2.44 g, yield 99%).

Nuclear magnetic data of compound 1-6: $^1H$ NMR (400 MHz, CDCl3) δ 6.63 (s, 2H), 5.99 (s, 1H), 4.09-4.04 (m, 2H), 2.78 (s, 3H), 2.94 (t, J=8 Hz, 2H), 1.75-1.68 (m, 2H), 1.43 (t, J=8 Hz, 3H), 0.99 (t, J=8 Hz, 4 Hz, 3H); $^{13}C$ NMR (100 MHz, CDCl3) δ 179.98, 167.00, 161.79, 159.84, 142.54, 116.43, 116.20, 111.08, 98.93, 63.95, 35.67, 23.05, 20.17, 14.70, 13.62.

2. Number and Structural Formula of the Target Compound

TABLE 1

| Serial number | Structural formula |
|---|---|
| 1-1 | ![structure] |
| 1-2 | ![structure] |
| 1-3 | ![structure] |
| 1-4* | ![structure] |
| 1-5 | ![structure] |
| 1-6* | ![structure] |

Note:
*Represents a new compound

3. Determination of the Activity of Compounds Inhibiting Tyrosinase

Method for determining the activity of inhibiting tyrosinase: Firstly, adding the sample: 40 μL (10% DMSO, setting different concentrations (0, 25, 50, 100, 200 μg/mL)) into a 96-well plate (aloesin is the positive control), then adding L-tyrosine: 40 μL (0.1 mg/mL, dissolving in 0.1M potassium phosphate buffer solution, pH=6.8), tyrosinase: 40 μL (48 U/mL, dissolving in 0.1M potassium phosphate buffer solution, pH=6.8), and finally diluting the volume to 200 μL with potassium phosphate buffer solution, and detecting the absorbance at 475 nm on 0 min; after incubating at 37° C. for 30 min, measuring the absorbance.

$$\text{Inhibition rate \%} = \frac{(A-B)-(C-D)}{A-B}$$

A: Absorbance of blank solution after incubation

B: Absorbance of blank solution before incubation

C: Absorbance of sample solution after incubation

D: Absorbance of sample solution before incubation

TABLE 2 series of compounds inhibit tyrosinase activity

| Compound No. | IC$_{50}$ ± SEM$^a$ (mM) |
|---|---|
| 1-1 | 9.3 ± 0.09 |
| 1-2 | 6.2 ± 0.07 |
| 1-3 | 2.4 ± 0.10 |
| 1-4 | 5.4 ± 0.03 |
| 1-5 | 0.2 ± 0.07 |
| 1-6 | 0.6 ± 0.03 |
| Aloesin | 2.7 ± 0.04 |

Note:
$^a$SEM is the mean standard deviation, aloesin is used as a positive control, n = 3.

The test results show that each said compound has tyrosinase inhibitory activity, wherein the tyrosinase inhibitory activity of the compounds 1-5 and 1-6 are higher than the tyrosinase inhibitory activity of aloesin. The activity is significantly improved after the 7-position hydroxyl is methylated or ethylated.

The above description is only the preferred embodiments of the present invention and is not intended to limit the present invention. Any modification, equivalent replacement, improvement, etc. made within the spirit and principle of the present invention shall be included in the scope of protection of the present invention.

The invention claimed is:

1. A 5-methylchromone, having the structure shown in formula (1):

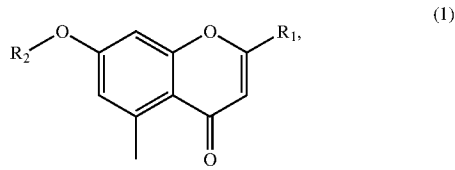

(1)

where R$_1$ is —CH$_2$CH$_2$CH$_3$ or —C(CH$_3$)$_3$, R$_2$ is H or —CH$_2$CH$_3$; and wherein when R$_1$ is —CH$_2$CH$_2$CH$_3$, R$_2$ is —CH$_2$CH$_3$.

2. The 5-methylchromone according to claim 1, having the structure shown in formula (1-6):

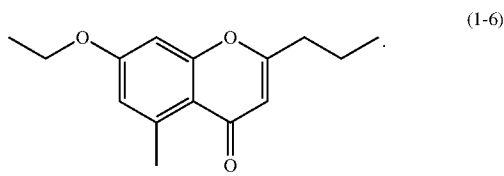 [SMILES: CCCc1cc(=O)c2c(C)cc(OCC)cc2o1]

(1-6)

3. The 5-methylchromone according to claim 1, having the structure shown in formula (1-4):

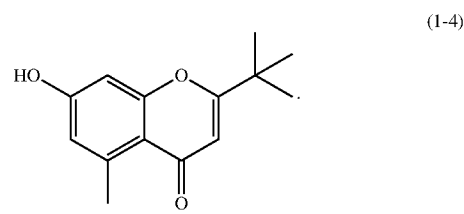 [SMILES: Cc1cc(O)cc2oc(C(C)(C)C)cc(=O)c12]

(1-4)

4. A preparation method of 5-methylchromone, having reaction formula:

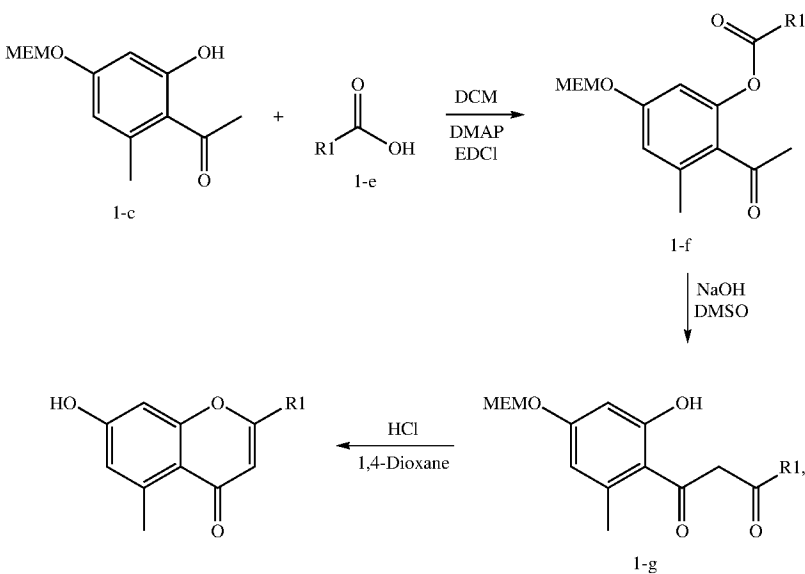

where $R_1$ is —$CH_3$, —$CH_2CH_3$, —$CH_2CH_2CH_3$, or —$C(CH_3)_3$;

the preparation method comprising:

dissolving the compound 1-c and the compound 1-e in the DCM, adding the DMAP, cooling to 0° C., adding the EDCI, raising to room temperature, and stirring to react; after the reaction being completed, extracting with ethyl acetate and water, taking the organic phase, concentrating under reduced pressure, and separating and purifying the residue by column chromatography, the purification solvent A being petroleum ether and ethyl acetate, obtaining the compound 1-f;

dissolving the compound 1-f in the DMSO, adding the NaOH, and stirring to react; after the reaction being completed, extracting with ethyl acetate and water, taking the organic phase, concentrating under reduced pressure, and separating and purifying the residue by column chromatography, the purification solvent B being petroleum ether and ethyl acetate, obtaining the compound 1-g;

dissolving compound the 1-g in the 1,4-dioxane, dripping concentrated hydrochloric acid solution, and stirring to react; after the reaction being completed, concentrating under reduced pressure, washing the residue with dichloromethane, obtaining the target compound; wherein if $R_1$ is —$CH_3$, it is obtained for a target compound 1-1; $R_1$ being —$CH_2CH_3$, obtained for a target compound 1-2;

if $R_1$ is —$CH_2CH_2CH_3$, it is obtained for a compound 1-3; $R_1$ being —$C(CH_3)_3$, obtained for the target compound 1-4.

5. The preparation method of 5-methylchromone according to claim 4, wherein, in condition that the $R_1$ is —$CH_3$, —$CH_2CH_3$, —$CH_2CH_2CH_3$, the purification solvent A is prepared from petroleum ether and ethyl acetate in a volume ratio of 7:1; the purification solvent B is prepared from petroleum ether and ethyl acetate in a volume ratio of 6:1;

in condition that the $R_1$ is —$C(CH_3)_3$, the purification solvent A is prepared from petroleum ether and ethyl acetate in a volume ratio of 8:1; the purification solvent B is prepared from petroleum ether and ethyl acetate in a volume ratio of 7:1.

6. A preparation method of 5-methylchromone, having reaction formula:

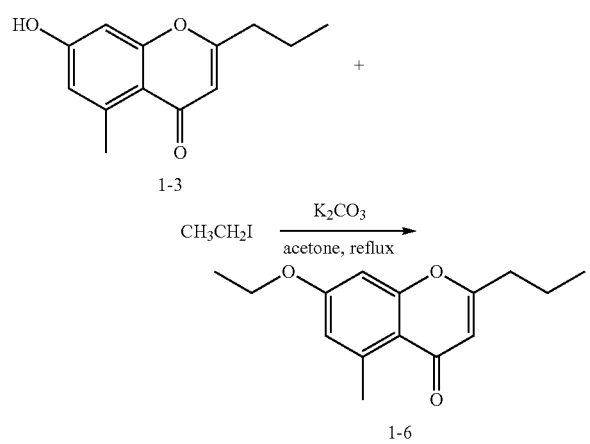

the preparation method comprising:

dissolving the compound 1-3 according to claim 4 and iodoethane in acetone, then adding $K_2CO_3$, heating to reflux and stirring to react; after the reaction being completed, concentrating under reduced pressure, separating and purifying the residue by column chromatography, the purification solvent being petroleum ether and ethyl acetate, obtaining the target compound 1-6.

7. A preparation method of 5-methylchromone, wherein the compound 1-3 according to claim 4 is reacted with iodomethane to obtain the compound 1-5, having reaction formula:

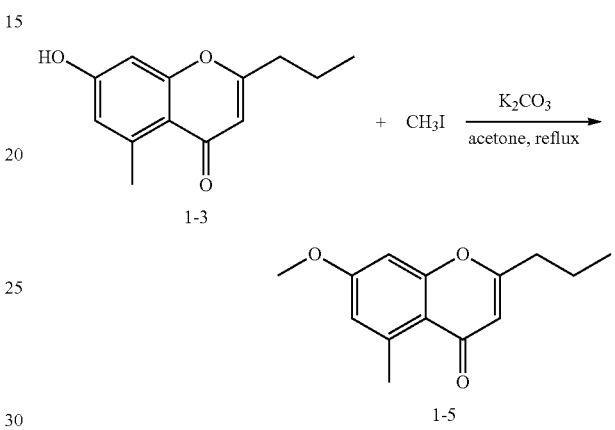

the preparation method comprising:

dissolving the compound 1-3 and iodomethane in acetone, adding $K_2CO_3$, heating reflux and stirring to react; after the reaction being completed, concentrating under reduced pressure, and separating and purifying the residue by column chromatography; the purification solvent being petroleum ether and ethyl acetate in a volume ratio of 6:1, obtaining the target compound 1-5.

8. A tyrosinase inhibitor or whitening agent comprising a compound as shown in the formula (1)

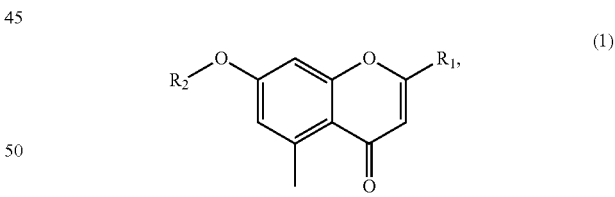

wherein $R_1$ is —$CH_3$, —$CH_2CH_3$, —$CH_2CH_2CH_3$ or —$C(CH_3)_3$, and $R_2$ is H, —$CH_3$ or —$CH_2CH_3$; and wherein when $R_1$ is —$CH_2CH_2CH_3$, $R_2$ is —$CH_3$ or —$CH_2CH_3$.

9. A tyrosinase inhibitor or whitening agent comprising the compound of claim 1.

10. A tyrosinase inhibitor or whitening agent comprising the compound of claim 2.

* * * * *